US008351567B2

(12) United States Patent  (10) Patent No.: US 8,351,567 B2
Wuestenbecker et al.  (45) Date of Patent: Jan. 8, 2013

(54) METHOD AND SYSTEM FOR THE AUTOMATED TESTING AND/OR MEASURING OF A PLURALITY OF SUBSTANTIALLY IDENTICAL COMPONENTS USING X-RAY RADIATION

(75) Inventors: Michael Wuestenbecker, Luetjensee (DE); Ingo Stuke, Reinfeld (DE)

(73) Assignee: GE Sensing & Inspection Technologies GmbH, Huerth (DE)

( * ) Notice: Subject to any disclaimer, the term of this patent is extended or adjusted under 35 U.S.C. 154(b) by 205 days.

(21) Appl. No.: 12/842,652

(22) Filed: Jul. 23, 2010

(65) Prior Publication Data

US 2011/0019796 A1   Jan. 27, 2011

(30) Foreign Application Priority Data

Jul. 24, 2009  (EP) .................................... 09009615

(51) Int. Cl.
*G01N 23/083* (2006.01)
*H05G 1/02* (2006.01)
*A61B 6/03* (2006.01)

(52) U.S. Cl. .............................. 378/57; 378/58; 378/193
(58) Field of Classification Search .................... 378/53, 378/57, 58, 193, 202, 203
See application file for complete search history.

(56) References Cited

U.S. PATENT DOCUMENTS

| 5,299,249 | A | * | 3/1994 | Burke et al. ..................... 378/15 |
| 5,982,844 | A | * | 11/1999 | Tybinkowski et al. ............ 378/4 |
| 6,035,014 | A | * | 3/2000 | Hiraoglu et al. ................ 378/57 |
| 6,236,709 | B1 | * | 5/2001 | Perry et al. ....................... 378/57 |
| 6,430,255 | B2 | * | 8/2002 | Fenkart et al. ................... 378/57 |
| 6,668,403 | B2 | * | 12/2003 | Seufert ............................. 5/601 |
| 6,859,518 | B2 | * | 2/2005 | Banchieri et al. ............... 378/57 |
| 7,072,434 | B1 | * | 7/2006 | Tybinkowski et al. ............ 378/4 |
| 7,261,466 | B2 | * | 8/2007 | Bhatt et al. ..................... 378/199 |
| 7,356,116 | B2 | * | 4/2008 | Anwar et al. .................... 378/57 |
| 7,384,194 | B2 | * | 6/2008 | Gatten ........................... 378/208 |
| 7,410,295 | B2 | * | 8/2008 | Distler et al. ................. 378/199 |
| 7,415,094 | B2 | * | 8/2008 | Johnson et al. ................. 378/57 |
| 7,492,855 | B2 | * | 2/2009 | Hopkins et al. ................. 378/10 |
| 7,492,860 | B2 | * | 2/2009 | Garms et al. .................... 378/57 |
| 7,869,566 | B2 | * | 1/2011 | Edic et al. ....................... 378/57 |
| 7,889,837 | B2 | * | 2/2011 | Takamatsu et al. ............. 378/19 |
| 2007/0133743 | A1 | | 6/2007 | Johnson et al. |
| 2008/0149864 | A1 | | 6/2008 | Hargrove |

FOREIGN PATENT DOCUMENTS

| DE | 19955937 | 5/2001 |
| WO | WO-99-19714 | 4/1999 |
| WO | WO-2007-131038 | 11/2007 |

* cited by examiner

*Primary Examiner* — Allen C. Ho
(74) *Attorney, Agent, or Firm* — Saliwanchik, Lloyd & Eisenschenk

(57) ABSTRACT

A method and system for automated testing and/or measurement of a plurality of substantially identical components by means of X-ray radiation comprises a testing/measuring device with an X-ray device, a protection cabin surrounding the testing/measuring device, a conveying device for continuously conveying components to or away from the testing/measuring device, and a control/evaluation unit, which is set up for automated control of the system and for evaluation of the X-ray signals. The testing/measuring device comprises a support and a rotor mounted on the support so as to be continuously rotatable, the X-ray device being arranged on the rotor and the conveying device being set up for serial conveying of the components through the rotor and the control/evaluation unit for computer tomographic evaluation of the X-ray signals.

22 Claims, 2 Drawing Sheets

METHOD AND SYSTEM FOR THE AUTOMATED TESTING AND/OR MEASURING OF A PLURALITY OF SUBSTANTIALLY IDENTICAL COMPONENTS USING X-RAY RADIATION

RELATED APPLICATION

The application claims priority under 35 U.S.C. §119(e) of European Patent Application No. 09 009 615.7, filed on Jul. 24, 2009, which is hereby incorporated by reference in its entirety.

BACKGROUND OF THE INVENTION

The invention relates to a method and system for the automated testing and/or measuring of a plurality of substantially identical components using X-ray radiation.

Such systems are used for example for automatic serial testing of castings, the system being connected into the manufacturer's production line (inline testing). With known systems of this type the X-ray source and detector are arranged on a multiaxial manipulator, wherein by means of simple radiography, X-ray images of the test object are recorded and evaluated. However, the projection of the volume of the tested component onto the X-ray image allows only limited conclusions to be drawn as to the internal structure of the component.

To obtain precise information about the three-dimensional internal structure of components, it is known to laboratory test individual components by means of high resolution microtomography systems. X-ray tube and detector are mounted on a fixed support so as to be adjustable about a plurality of translational axes and the component is rotated about a vertical axis by means of a rotary table. Such systems are not suitable for automatic serial inline testing of components, in particular because the long period of time required for handling and high resolution investigation of a component is incompatible with the cycle times in a production line.

BRIEF SUMMARY OF THE INVENTION

It is the object of the invention to provide a method and system suitable for inline testing of components, with which information about the internal structure of the components may be obtained.

Embodiments of the subject invention achieve this object with the means to be found in the independent claims. Computer tomographic evaluation of the signals in response to X-rays makes it possible, in a manner known per se, to obtain information about the three-dimensional internal structure of the components, for example the precise location and shape of air inclusions in castings. Arrangement of the X-ray device on a continuously rotatable rotor makes it possible to convey the components through the rotor serially during testing; an additional manipulator such as, for example, a rotary table is unnecessary. In this way automatic serial investigation of components may be performed in a short period, which is compatible with the cycle times on a production line.

Embodiments of the subject invention are different from methods and systems for testing items of luggage, for which evaluation has to be set extremely broadly to cover any desired luggage contents. Instead, the system according to embodiments of the subject invention for investigating a plurality of substantially identical components may be appropriately tailored to the component type to be tested, or to a mix of a limited number of component types. These systems are therefore completely differently configured in particular in terms of X-ray parameters and evaluation algorithms. The testing/measuring system according to embodiments of the subject invention is expediently set up for automatic identification of material defects, such as gas inclusions, porosity or material inclusions of higher density in a substantially homogeneous material. The system according to embodiments of the subject invention may, however, additionally or alternatively be used for materials testing for measuring internal and external component structures (metrology). It is then optionally possible to dispense with a separate coordinate measuring machine.

Preferably, the method and system is set up to achieve a volume resolution in the X-ray image of less than or equal to 1 mm. In this way too, embodiments of the subject invention may be distinguished from systems for testing items of luggage, which generally operate with a resolution of several mm.

To achieve sub-mm-resolution, the conveying device preferably comprises, in the region of the annular unit, a conveying means with a substantially constant rate of advance. Substantially constant preferably means that fluctuations in rate of advance amount to at most 10%, preferably at most 5%.

With regard to the rough conditions prevailing in manufacturing environments, for example foundries, the protection cabin is preferably sealed in substantially airtight manner against the surrounding environment, in order to prevent penetration of dust and moisture into the protection cabin and the testing/measuring device arranged therein. To prevent penetration of dust and dirt through the openings for conveying the components in and out, the system preferably comprises a pipe connecting the two openings, extending through the rotor and defining a closed conveying duct, which additionally is preferably connected in airtight manner to the protection cabin. Furthermore, a cooling unit is preferably provided for cooling the interior of the protection cabin. Finally, the system preferably comprises a means for pressurising the protection cabin relative to the surrounding environment. Preferably the protection cabin is set up to shield the surrounding environment against X-ray radiation, in particular by means of an X-ray-absorbing layer, for example containing lead.

Preferably the conveying device comprises a conveyor belt guided without interruption through the testing/measuring device and largely transparent to radiation, thereby preventing problems related to a measurement gap in the conveying device in a simple manner.

Preferably the conveying device is height-adjustable in the region of the testing/measuring device for adaptation to components with different dimensions, so that the components may be passed through the testing/measuring device substantially centralized in height.

Embodiments of the subject invention are illustrated below by means of advantageous embodiments with reference to the attached Figures.

DETAILED DESCRIPTION OF THE INVENTION

Figure 1:
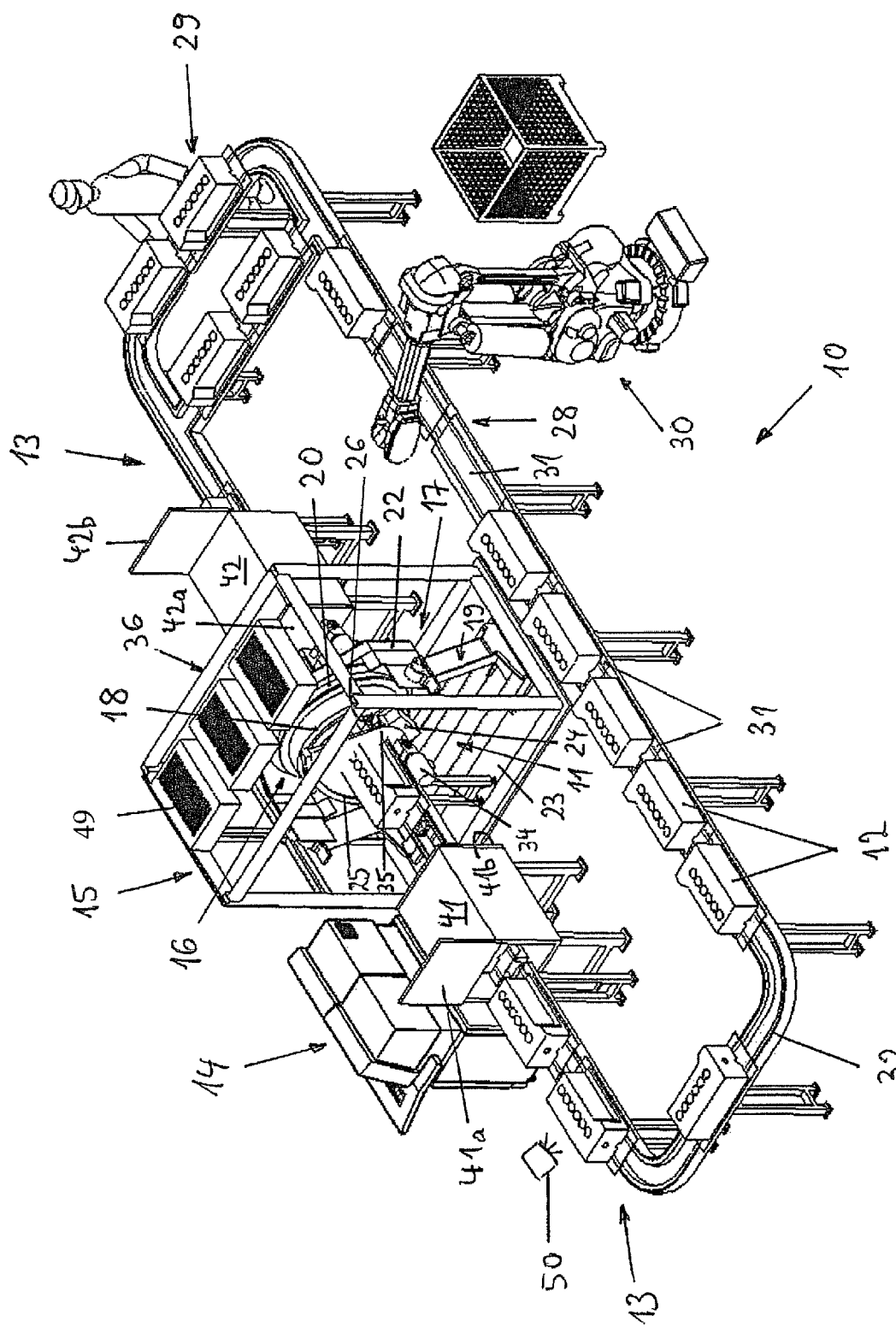
FIG. 1 shows a system for testing components in a production line.

Referring to FIG. 1, the system 10 comprises a testing/measuring device 11, a conveying device 13 for conveying a plurality of substantially identical components 12 to be tested serially to and away from the testing/measuring device 11, a control/evaluation unit 14 and a protection cabin 15 surrounding the testing/measuring device 11. Testing/measuring device should here be understood to mean testing and/or measuring device. The testing/measuring system 10 is suitable for connecting into a production line for example in a foundry for metallic castings 12.

Figure 2:
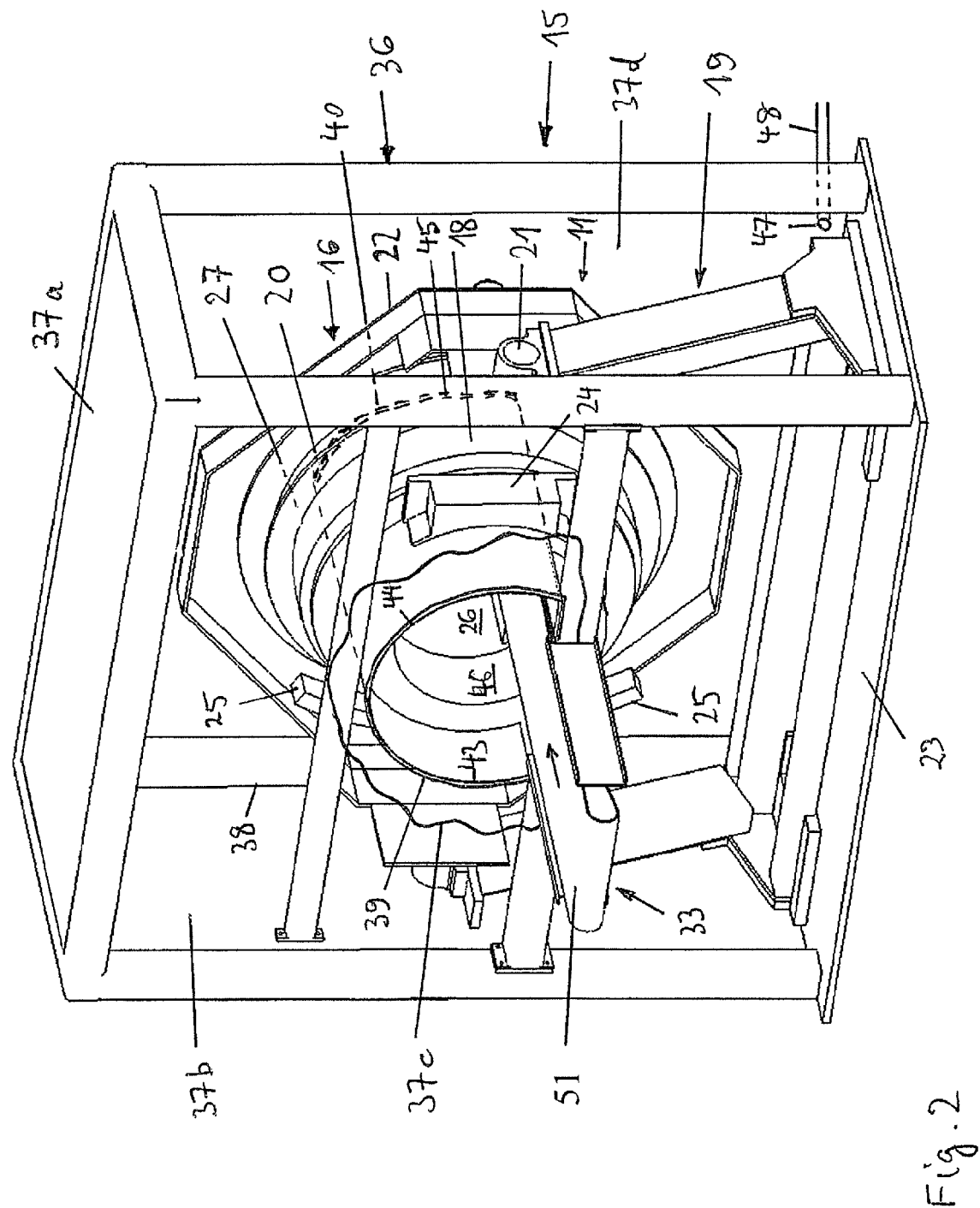
FIG. 2 shows another embodiment of a device for testing components.

The testing/measuring device 11 comprises a support 17 fixed during testing and an annular rotor 18. The support 17 comprises a pedestal 19 anchored to a base plate 23 and an annular supporting element 22 resting on said pedestal, here in the form of an octagonal plate. The annular supporting element 22 forms an annular rotational bearing 20 for the rotor 18. Rotational bearing 20, rotor 18 and optionally supporting element 22 form an annular unit 16, which comprises a central annular opening 26 for conveying components 12 through the annular unit 16. In order to allow horizontal orientation, the annular unit 16, as shown in FIGS. 1 and 2, may be inclined by means of a horizontal swivel bearing 21 for example in a range of +−30° relative to the pedestal 19, see embodiments according to FIGS. 1 and 2. The components 12 are preferably conveyed in an axially parallel manner, i.e. parallel to the rotor axis, through the rotor 18.

An X-ray tube 24 and an X-ray detector 25 are fastened opposite one another on the rotor 18. The X-ray tube 24, which preferably takes the form of a rotary anode tube, is preferably of the fan beam or cone beam type. The X-ray tube 24 is conveniently set up to illuminate the entire detector 25 and for this purpose preferably has in one direction a beam angle of at least 40°, preferably at least 60°. To achieve sub-mm image resolution the focus size of the X-ray beam is preferably below 1 mm, more preferably below 0.7 mm. The tube 24 is preferably operated with at least 80 kV of energy, more preferably at least 100 kV, more preferably at least 120 kV, for example approximately 140 kV. If a high penetration capacity is preferred, higher X-ray energies of up to 450 kV are feasible. To reduce the duration of testing and/or measuring, the X-ray tube 24 is preferably operated with a continuous output of at least 1 kW. To avoid problems due to excessive heat generation, the continuous output preferably amounts to less than 10 kW.

In an embodiment which is not shown, only the tube 24 may be fastened to the rotor 18, while the stationary detector 25 forms a 360° ring.

The X-ray detector 25 is preferably digital, with direct conversion of the impinging X-ray radiation into electrical counts; preferably it is a line scanning detector with a plurality of preferably at least 16 parallel lines. The detector 25 preferably comprises a length which is sufficient to detect the largest possible angular range of X-ray radiation emitted by the tube 24. It is preferably bent into a banana shape, such that the sensitive area is at a substantially constant distance from the source point of the X-ray tube 24 as far as possible everywhere. To achieve sub-mm image resolution the pixel size of the detector 25 amounts to at most 1 mm, preferably at most 0.7 mm.

The correction conveniently performed in the control/evaluation unit 14 to compensate the beam hardening effect is adjusted to the investigation of typical materials, for example metals, alloys, composite materials, aluminium, iron, et cetera.

During X-ray testing of a component 12 the rotor 18 is rotated continuously by means of rotary drives (not shown) fastened to the supporting element 22 about the central longitudinal axis of the annular unit 16, wherein a large number of full 360° revolutions of the rotor 18 are carried out per component 12. Electricity is supplied to the X-ray tube 24 and X-ray detector 25 rotating with the rotor 18 by means of a slip ring arrangement 27 arranged between the rotor 18 and the supporting element 22. The axis of rotation of the rotor 18 or the longitudinal axis of the annular unit 16 is oriented substantially parallel to the direction in which the components are conveyed through the testing/measuring device 11, preferably substantially horizontal.

The conveying device 13 preferably takes the form, as in the exemplary embodiment according to FIG. 1, of a conveyor line, i.e. of a translational conveyor. For connection into a production line for the components 12, the conveyor line comprises a loading section 28 and an unloading section 29. Loading of the conveyor line 13 proceeds in the exemplary embodiment according to FIG. 1 by means of a robot 30, while unloading is effected manually. It goes without saying that loading and unloading may also proceed otherwise.

In the exemplary embodiment according to FIG. 1 the conveying device 13 comprises conveying carriages 31 for accommodating one component 12, respectively, and at least one rail 32 along which the conveying carriages 31 are guided displaceably. The conveying device 13 may however also be differently constructed, in particular using conveyor belts.

The conveying device 13 is preferably set up to convey the components 12 through the testing/measuring device 11 at a substantially constant rate of advance, i.e. with fluctuations in the rate of advance of less than 10%, preferably less than 5%. To this end the conveying device 13 preferably comprises a separate drive 34 in the region of the testing/measuring device 11, preferably with servomotors, to achieve the required constant rate of advance. Accordingly, the drive 34 for conveying through the testing/measuring device 11 appropriately displays a more constant rate than other drives (not shown) for conveying to and away from the testing/measuring device 11.

In the preferred embodiment according to FIG. 2 a separate conveying means 33 with a continuous, uninterrupted conveying means 51, in particular a conveyor belt, is provided for conveying the components 12 through the testing/measuring device 11. The conveying means 51 is expediently substantially transparent to X-ray radiation. The continuous, uninterrupted, largely radiation-transparent conveying means 51 has the advantage that the conveying means 51 does not have to comprise any gap for allowing the X-ray radiation through.

On the other hand, in the embodiment according to FIG. 1 the conveying device 13 passes into the testing/measuring device 11 from both sides, such that the smallest possible gap 35 remains for unhindered passage of X-ray radiation. In this case an embodiment of the conveying device 13 with rail 32 and conveying carriages 31 in the region of the testing/measuring device 11 is advantageous, because the conveying carriages 31 allow bridging of the gap in a manner which is precise with regard to position and rate of advance.

In accordance with the above, the conveying device 13 is of translational construction over the entire conveying distance between the loading section 28 and the unloading section 29. It is therefore possible to dispense with elaborate carousel-like pivoting conveyors for conveying the components 12 from the conveyor line 13 to the testing/measuring device 11 and back. Other manipulation of the components 12, for example rotation of the components 12 about a vertical axis during X-ray investigation, may be dispensed with.

The translational conveyance, occurring during testing, of the component 12 to be tested through the testing/measuring device 11 parallel to the axis of rotation of the rotor 18 and the simultaneous continuous rotation of the X-ray system 24, 25 about the component 12 to be tested results in an overall helical movement of the X-ray system 24, 25 about the component 12 to be tested. The control/evaluation unit 14 comprises a rapid CT reconstruction algorithm for converting the recorded X-ray data from the helical geometry into a volume or voxel representation. The control/evaluation unit 14 further comprises an algorithm for analysing the volume image depending on the intended application. This may in particular comprise automatic identification of internal defects or anomalies of the component 12, for example air inclusions, using predetermined test parameters which are known in principle and do not therefore have to be explained in greater detail. Every component may optionally be classified as "compliant" or "non-compliant" and optionally marked optically accordingly or automatically rejected. Finally, the control/evaluation unit 14 may comprise a communication unit for data transmission with an external unit, for example the central control unit of the manufacturing plant.

In addition or as an alternative to the helical scanning mode, the control/evaluation unit 14 may also perform axial scans and/or scans of just one part of a component 12, for example individual slices or at specific positions.

Alternatively or in addition, for the identification of internal defects or anomalies of the component 12 the control/evaluation unit 14 may also be set up to determine the three-dimensional geometric dimensions of the components 12, i.e. internal and external component structures, from the X-ray data. It is then optionally possible to dispense with a separate coordinate measuring device.

To shield the surrounding environment against the X-ray radiation generated by the X-ray tube 24, the system 10 comprises a radiation protection cabin 15 surrounding the testing/measuring device 11. The radiation protection cabin 15 comprises a frame 36, which may consist for example of metal tubes or rods, and plate-shaped wall elements 37a, 37b, 37c, 37d etc., which are merely indicated in FIG. 2 for the top wall 37a, the side wall 37b remote from the observer, the front wall 37c facing the observer through which the components 12 are conveyed into the protection cabin 15, and the rear wall 37d remote from the observer through which the components 12 are conveyed out of the protection cabin 15. The wall elements 37 contain an X-ray-absorbing, in particular lead-containing, layer of sufficient thickness.

An inlet opening 39 and a corresponding outlet opening 40 are provided in the wall elements 37c, 37d for conveying the components 12 through the protection cabin 15. Each passage opening 39, 40 in each case has a passage lock 41, 42 associated with it, which comprises a slide 41a, 42a, respectively, for closing an inlet opening of the passage lock 41, 42 and a slide 41b, 42b, respectively, for closing an outlet opening of the passage lock 41, 42. The passage locks 41, 42 and the slides 41a, 41b, 42a, 42b are likewise set up for substantially complete absorption of X-ray radiation. In operation one slide 41a, 41b or 42a, 42b, respectively, of a passage lock 41, 42 is closed at all times, such that radiation protection is ensured at all times.

To prevent penetration of dust and moisture into the protection cabin 15, the latter is closed in airtight manner, for example with the aid of sealing elements 38 between the wall elements 37, the frame 36 and the base plate 23. To achieve a substantially completely sealed interior for the testing/measuring device 11, i.e. apart from any air-conditioning openings, a conveniently substantially radiation-transparent pipe 43 is provided, which extends through the protection cabin 15 from one passage opening 39 to the other passage opening 40 and passes through the annular opening 26 in the annular unit 16. The conveying device 13 passes through the pipe 43 in the region of the testing/measuring device 11, said pipe defining a conveying duct 46 or conveying tunnel. The pipe 43 is preferably free of openings in the pipe wall, such that dirt particles transported with the conveying device 13 or the components 12 arranged thereon cannot enter the testing/measuring device 11. At its ends the pipe is preferably connected in airtight manner with the wall elements 37c, 37d at the edge defining the passage openings 39, 40, in particular with the aid of corresponding sealing elements 44, 45. The diameter of the pipe 43 is conveniently adapted to the internal diameter of the annular unit 16, in order to allow testing of the largest possible components 12. In accordance with the above, the testing/measuring device 11 is substantially completely enclosed in the protection cabin 15.

In order to dissipate the heat generated when the testing/measuring device 11 is in operation and keep the interior of the protection cabin 15 at a sufficiently low operating temperature even in very warm environments, for example a foundry, at least one temperature-controlled, in particular electrically operated cooling unit 49, for example an air-conditioning system, is fitted to the protection cabin 15.

So that no dust/moisture can enter the protection cabin 15 in the case of any leaks, and through any functional openings such as for example an exhaust air opening for the air-conditioning system 49, a means is preferably provided for pressurising the cabin 15. This may for example be a compressed air connection 47, which may be connected to an external compressed air source via a compressed air line 48. Pressurisation may alternatively also proceed by way of the cooling unit 49.

As a result of the protection cabin 15 and the pipe 43, which also protects the annular unit 16 from damage by malpositioned components 12, no separate housing is needed for the annular unit 16. Dispensing with such a housing for the annular unit 16 in turn simplifies heat removal from the annular unit 16.

The conveying device 13 may be height-adjustable in the region of the testing/measuring device 11 for adaptation to components 12 with different dimensions, so that the components 12 may be passed through the annular unit 16 substantially centrally.

The system 10 may optionally comprise a device 50 connected upstream of the testing/measuring device 11 for identifying the component type for example with the aid of an optical camera and an image recognition algorithm. As a function of the result of the identification, parameters of the measuring/testing device 11 may be adjusted to the respective component type and/or the result of the X-ray investigation may be related to the individual component 12, for example by means of the serial number. Alternatively, identification of the component type may also be effected from the three-dimensional X-ray image by means of a corresponding recognition algorithm.

We claim:

1. A system for automated testing and/or measurement of a plurality of substantially identical components via X-ray radiation, comprising:

a testing/measuring device with an X-ray device, wherein the X-ray device comprises an X-ray source for generating X-rays and an X-ray detector for detecting X-rays and producing signals in response to X-rays;

a protection cabin surrounding the testing/measuring device;

a conveying device for continuously conveying a plurality of components to or away from the testing/measuring device; and a control/evaluation unit, which is set up for automated control of the system and for evaluation of the signals in response to X-rays, wherein the testing/measuring device comprises a support and a rotor mounted on the support so as to be continuously rotatable, the X-ray device being arranged on the rotor and the conveying device being set up for serial conveying of the components through the rotor and the control/evaluation unit being set up for computer tomographic evaluation of the signals in response to X-rays, wherein the protection cabin is sealed in a substantially airtight manner against the surrounding environment.

2. The system according to claim 1, further comprising a pipe extending through the rotor and defining a conveying tunnel.

3. The system according to claim 2, wherein the pipe is connected in airtight manner to the protection cabin.

4. The system according to claim 1, further comprising a cooling unit for cooling the interior of the protection cabin.

5. The system according to claim 1, further comprising a means for pressurising the protection cabin.

6. The system according to claim 1, wherein the protection cabin is set up to shield the surrounding environment against X-ray radiation.

7. The system according to claim 1, wherein the control/evaluation unit is set up for individual adjustment of operating parameters of the system, depending on the type of components to be tested or measured.

8. The system according to claim 1, wherein the control/evaluation unit is set up for automatic identification of one or more material defects.

9. The system according to claim 8, wherein the control/evaluation unit is set up for automatic identification of gas inclusions.

10. The system according to claim 8, wherein the control/evaluation unit is set up for automatic identification of porosity.

11. The system according to claim 8, wherein the control/evaluation unit is set up for automatic identification of material inclusions of higher density in a substantially homogeneous material.

12. The system according to claim 1, wherein the system is set up to achieve a resolution in an X-ray image of less than or equal to 1 mm.

13. The system according to claim 1, wherein the conveying device is set up to convey the components at a substantially constant rate of advance in a region of the testing/measuring device.

14. The system according to claim 1, wherein the conveying device comprises a conveyor belt guided without interruption through the testing/measuring device.

15. The system according to claim 1, wherein the conveying device is height-adjustable in a region of the testing/measuring device.

16. The system according to claim 1, wherein the X-ray source is operated with a voltage of at least 80 kV.

17. The system according to claim 1, wherein the X-ray source is operated with a continuous power of at least 1 kW.

18. The system according to claim 1, wherein the plurality of components are substantially identical.

19. A system for automated testing and/or measurement of a plurality of substantially identical components via X-ray radiation, comprising:

a testing/measuring device with an X-ray device, wherein the X-ray device comprises an X-ray source for generating X-rays and an X-ray detector for detecting X-rays and producing signals in response to X-rays;

a protection cabin surrounding the testing/measuring device;

a conveying device for continuously conveying a plurality of components to or away from the testing/measuring device; and a control/evaluation unit, which is set up for automated control of the system and for evaluation of the signals in response to the testing/measuring device comprises a support and a rotor mounted on the support so as to be continuously rotatable, the X-ray device being arranged on the rotor and the conveying device being set up for serial conveying of the components through the rotor and the control/evaluation unit being set up for computer tomographic evaluation of the signals in response to X-rays, further comprising a pipe extending through the rotor and defining a conveying tunnel.

20. The system according to claim 19, wherein the pipe is connected in airtight manner to the protection cabin.

21. A method for automatically testing and/or measuring a plurality of substantially identical components via X-ray radiation, comprising:

providing:
a testing/measuring device with an X-ray device, wherein the X-ray device comprises an X-ray source for generating X-rays and an X-ray detector for detecting X-rays and producing signals in response to X-rays;

a protection cabin surrounding the testing/measuring device;

a conveying device for continuously conveying a plurality of components to or away from the testing/measuring device; and a control/evaluation unit, which is set up for automated control of the system and for evaluation of the signals in response to X-rays, wherein the testing/measuring device comprises a support and a rotor mounted on the support so as to be continuously rotatable, the X-ray device being arranged on the rotor and the conveying device being set up for serial conveying of the components through the rotor and the control/evaluation unit being set up for computer tomographic evaluation of the signals in response to X-rays;

continuously conveying the plurality of components to or away from the testing/measuring device and through the rotor;

generating X-rays via the X-ray source and radiating each of the plurality of components with the generated X-rays;

detecting X-rays from the irradiated components via the X-ray detector;

producing signals in response to X-rays from the detected X-rays via the X-ray detector; and evaluating the signals in response to X-rays via computer tomographic evaluation via the control/evaluation unit, wherein the protection cabin is sealed in a substantially airtight manner against the surrounding environment.

22. The method according to claim 21, wherein providing the conveying device for continuously conveying a plurality of components to or away from the testing/measuring device comprises providing a pipe extending through the rotor and defining a conveying tunnel.

* * * * *